United States Patent [19]

Landry

[11] Patent Number: 5,738,516

[45] Date of Patent: Apr. 14, 1998

[54] ADJUSTABLE MOUNTING DEVICE FOR A DENTAL ARTICULATOR

[76] Inventor: Alain Landry, 4369 Ave. des Fauvettes, Charlesbourg, Québec, Canada, G1G 4S5

[21] Appl. No.: 768,080

[22] Filed: Dec. 16, 1996

[51] Int. Cl.⁶ .................................................. A61C 11/00
[52] U.S. Cl. ...................................... 433/60; 433/63
[58] Field of Search ................................ 433/60, 63, 65

[56] References Cited

U.S. PATENT DOCUMENTS

| | | | |
|---|---|---|---|
| 2,731,723 | 1/1956 | Brandhandler | 433/60 |
| 2,754,588 | 7/1956 | Cordell | 433/60 |
| 3,844,040 | 10/1974 | Willis | 433/60 |
| 4,058,895 | 11/1977 | Mack et al. | 433/32 |
| 4,214,367 | 7/1980 | Mack et al. | 433/60 |
| 4,391,589 | 7/1983 | Monfredo et al. | 433/63 |
| 4,460,338 | 7/1984 | Mercer et al. | 433/60 |
| 4,496,319 | 1/1985 | Steinbock | 433/57 |
| 4,687,442 | 8/1987 | Wong | 433/60 |
| 4,734,033 | 3/1988 | Huffman | 433/60 |
| 4,923,398 | 5/1990 | Mackman | 433/60 |
| 5,044,949 | 9/1991 | Xanthopoulos | 433/58 |
| 5,064,372 | 11/1991 | Edwardson | 433/66 |
| 5,190,455 | 3/1993 | Schreiber | 433/54 |
| 5,378,148 | 1/1995 | Mogensen | 433/64 |

OTHER PUBLICATIONS

Hanau Articulators (various models) from product circulars.
SAM 3 Articulator & Axioquick Facebow Manual.
Hanau Series H2 and 145 Articulators, technique for full denture prosthodontics. Company: Teledyne Hanau: P.O.Box 203, 80 Sonwil Drive, Buffalo, N.Y. 14225, USA.

*Primary Examiner*—John J. Wilson
*Attorney, Agent, or Firm*—Lowe, Price, LeBlanc & Becker

[57] ABSTRACT

The adjustable mounting device comprises two superposed plates in sliding relationship. One of the plates is pivotally connected to the articulator. A first mechanism is provided to selectively slide and lock in position one of the plates relative to the other while this other plate is provided with a second mechanism to selectively rotate and lock the device in position with reference to the dental articulator. This mounting device replaces one or both conventional fixed mounting plates in a dental articulator to provide adjustability between the lower and upper parts of the dental cast.

3 Claims, 5 Drawing Sheets

ADJUSTABLE MOUNTING DEVICE FOR A DENTAL ARTICULATOR

BACKGROUND

Dental articulator have been known in the art for many years now. Numerous examples can be found in patents, such as in U.S. Pat. Nos. 4,496,319, 5,064,372 and 5,190, 455. In brief, a dental articulator (sometimes called "mandibular position variator") is used to simulate the movement of the mandible relative to the maxilla using a two-part dental cast of a patient. Each part of the dental cast is mounted in the dental articulator by means of a corresponding mounting plate on which it adheres. The mounting plates are connected to respective arms of the dental articulator by thumbscrews.

A common problem with mounting plates used hitherto is that they are fixed and it is thus difficult, for instance, to change the initial relative position of the opposite dental cast parts.

SUMMARY

The object of the present invention is to provide a mounting device that replaces one or both conventional fixed mounting plates in a dental articulator to provide adjustability between the lower and upper parts of the dental cast.

More particularly, the object of the present invention is to provide an adjustable mounting device for use with a dental articulator, the mounting device comprising:

a plate having two opposite sides, one side being pivotally connectable to the dental articulator; and a mechanism to selectively rotate and lock in position the plate relative to the dental articulator.

It is another object of the present invention to provide an adjustable mounting device for use with a dental articulator, the mounting device comprising:

a first plate having opposite first and second sides;

a second plate having opposite first and second sides, the first side of the second plate being superposed to the first side of the first plate and in sliding relationship therewith, the second side of the second plate being connectable to the dental articulator; and a mechanism to selectively slide and lock in position the first plate relative to the second plate.

It is also an object of the present invention to provide an adjustable mounting device for use with a dental articulator, the mounting device comprising:

a first plate having opposite first and second sides;

a second plate having opposite first and second sides, the first side of the second plate being superposed to the first side of the first plate and in sliding relationship therewith, the second side of the second plate being pivotally connectable to the dental articulator;

a first mechanism to selectively slide and lock in position the first plate relative to the second plate; and a second mechanism to selectively rotate and lock in position the second plate relative to the dental articulator.

A non restrictive description of preferred embodiments will now be given with reference to the appended drawings.

IDENTIFICATION OF THE COMPONENTS

Figure 1:
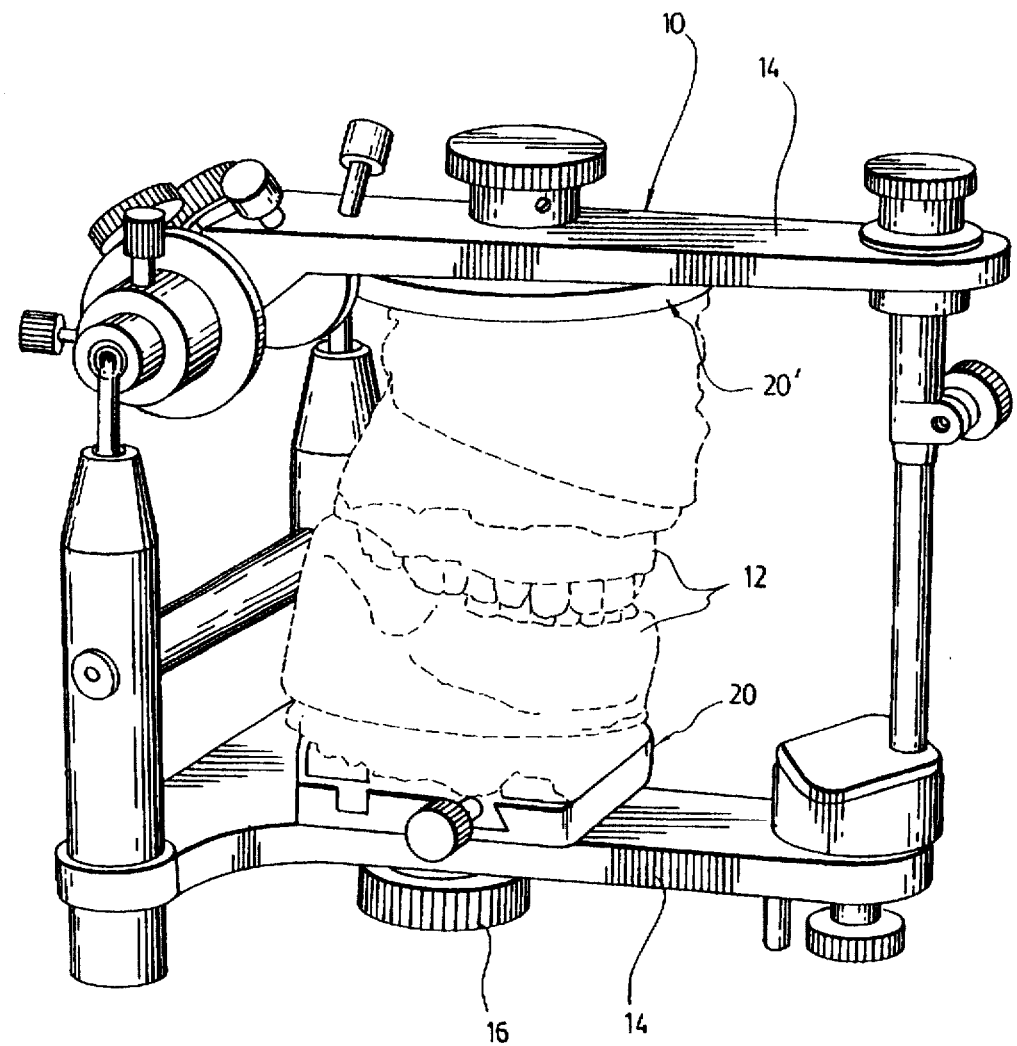
FIG. 1 is a side perspective view of a mounting device according to a possible embodiment of the present invention, showing one mounting device installed in a dental articulator and bearing a corresponding part of a dental cast.
Figure 2:
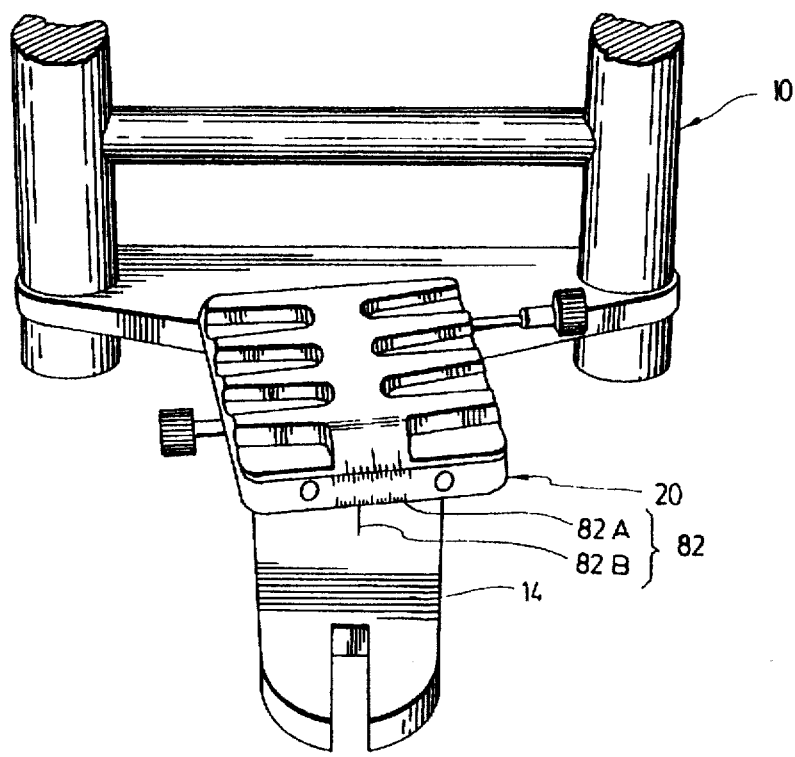
FIG. 2 is a front perspective view of the mounting device in FIG. 1, showing an example of an angular displacement of the device with reference to the dental articulator.

The following is a list of the reference numerals, along with the names of the corresponding elements, that are used in the appended drawings and in the description.

- 10 dental articulator
- 12 dental cast
- 14 arms (of the dental articulator)
- 16 pivot screw (thumbscrew)
- 18 pegs
- 20 mounting device
- 20' mounting plate (PRIOR ART)
- 30 first plate
- 32 first side (of the first plate)
- 34 second side (of the first plate)
- 36 recesses
- 38 tenon
- 39 flange
- 40 second plate
- 42 first side (of the second plate)
- 44 second side (of the second plate)
- 46 pivot bore
- 48 opening
- 50 mortise
- 52 slot
- 60 first mechanism
- 62 first screw
- 64 threaded element
- 66 longitudinal opening (of the tenon 38)
- 70 second mechanism
- 72 second screw
- 74 holding element
- 76 slot
- 80 first graduated scale
- 80A, 80B vernier
- 82 second graduated scale
- 82A, 82B vernier

DESCRIPTION

Referring to FIG. 1, there is shown an example of a dental articulator (10). A two-part dental cast (12) is located between arms (14) of the articulator (10). FIG. 1 shows the lower part of the dental cast (12) held by a mounting device (20) according to a preferred embodiment of the present invention, while the upper part of the dental cast (12) is held by a conventional mounting plate (20') as found in the prior art. In both instances, they are connected to the corresponding arms (14) of the articulator (10) by means of thumbscrews (16). Of course, the positions of the mounting device (20) and the mounting plate (20') can be inverted. It is also possible to use two mounting devices (20) on the same articulator (10), one holding the upper part of the dental cast (12) while the other is holding the lower part thereof. These two mounting devices (20) may also be two different models, depending on the specific needs.

There are several embodiments for the present invention, all of which allow at least one part of the dental cast (12) to be moved relative to the other. The embodiment shown in FIGS. 1 to 7 combines every element needed for building the various other embodiments.

Figure 3:
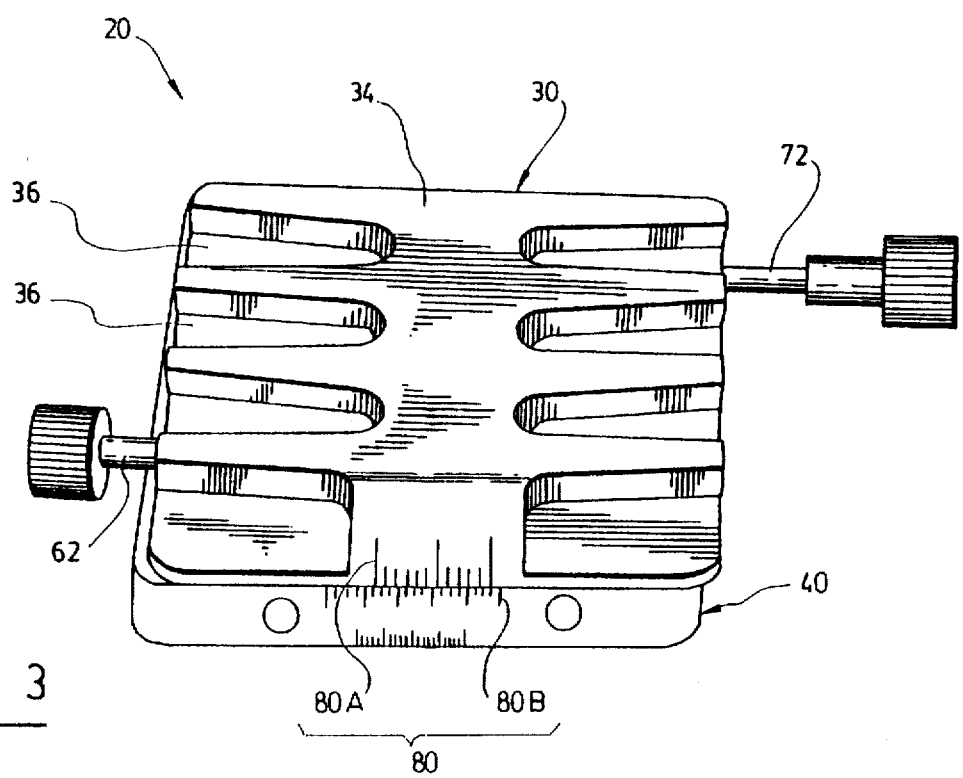
FIG. 3 is an enlarged front perspective view of the mounting device in FIG. 1, showing an example of a relative sliding movement between the plates.
Figure 4:
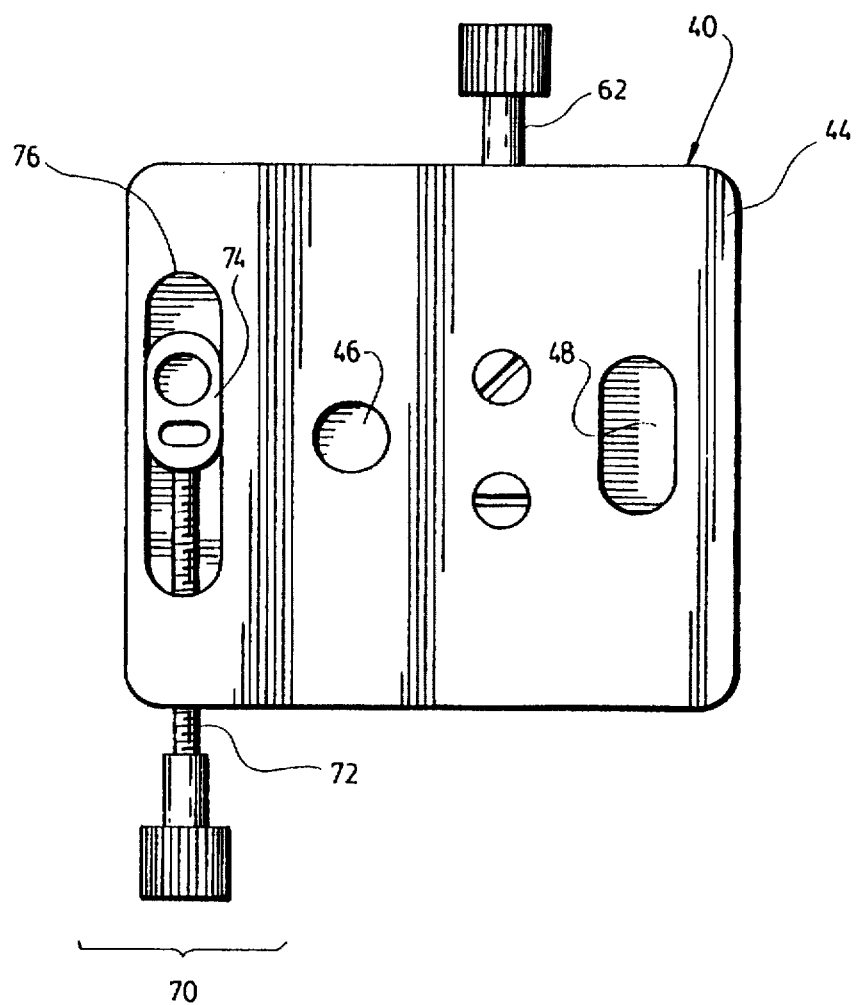
FIG. 4 is a bottom view of the second plate of the mounting device shown in FIG. 1.

The mounting device (20) may be moved according to two main degrees of freedom, one being a rotation around the vertical axis (FIG. 2) and the other being a translation in the horizontal plane (FIG. 3). The various embodiments are subcombinations of these movements. The embodiment shown in the drawings will be first explained.

Figure 7:
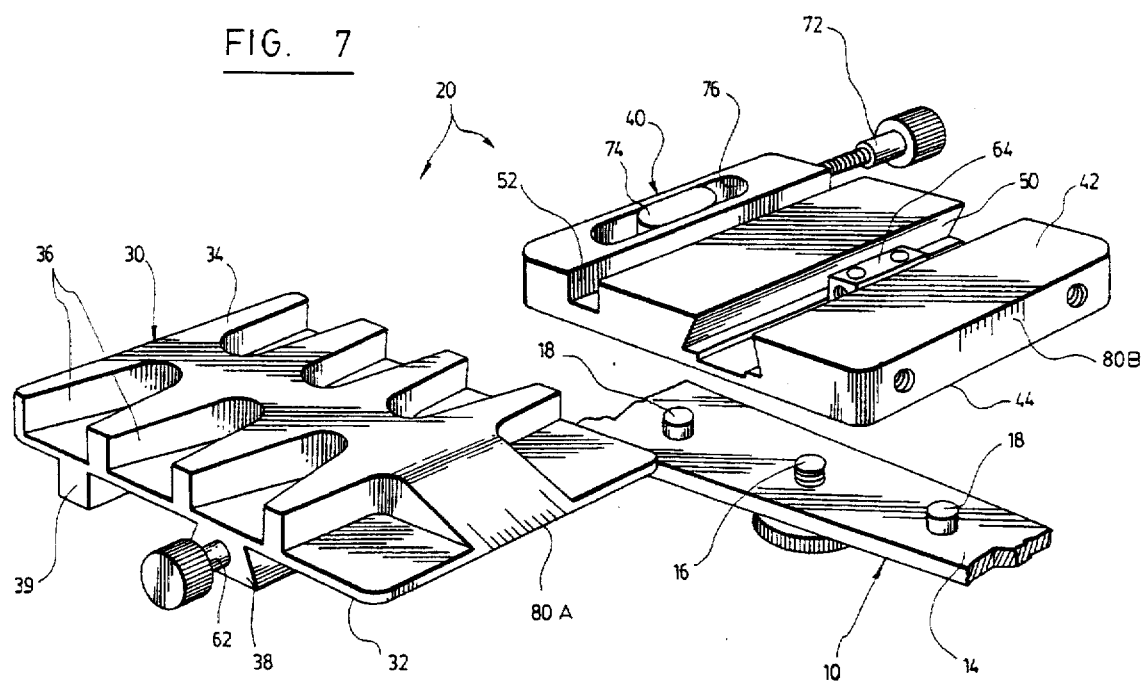
FIG. 7 is a side exploded perspective view of the mounting device shown in FIG. 1.

As best shown in FIG. 7, the mounting device (20) comprises a first plate (30) superposed to a second plate (40) in a sliding relationship. The first plate (30) has a first side (32) and a second side (34) opposite the first side (32). The second plate (40) also has a first side (42) and a second side (44) opposite the first side (42). The first side (32) of the first plate (30) is interconnected to the first side (42) of the second plate (40) as further explained hereinafter. As for the second side (34) of the first plate (30), it preferably comprises a plurality of recesses (36) on which the corresponding part of the dental cast (12) adheres. The recesses (36) provide an increased surface for the plaster that holds the dental cast (12).

The present embodiment of the mounting device (20) combines the aforesaid two degrees of freedom. The first degree of freedom is the relative sliding movement in one direction between the first (30) and the second plate (40). This direction is preferably the lateral direction with reference to the articulator (10) but any other may be chosen. The second degree of freedom is the relative rotation between the second plate (40) and the corresponding arm (14) of the articulator (10) on which the second side (44) of the second plate (40) is pivotally connected (see FIG. 2). Of course, the first plate (30) is also rotated at the same time since it is supported by the second plate (40). The pivot attachment between the second plate (40) and the corresponding arm (14) is preferably achieved by a threaded pivot bore (46) located on the second side (44) of the second plate (40). The pivot screw (16), projecting out of a hole in the corresponding arm (14), is screwed into to bore (46) but not too tight in order to allow the rotation.

As best shown in FIG. 3, the first (30) and the second plates (40) are interconnected in a sliding relationship. This is preferably achieved by a dovetail-like tenon (38) projecting from the first side (32) of the first plate (30). The tenon (38) fits into a corresponding mortise (50). Additionally, a flange (39) also projects from the first side (32) of the first plate (30) and extends parallel to the tenon (38). The flange (39) fits into a corresponding slot (52).

A first mechanism (60) is provided to selectively slide and lock in position the first plate (30) relative to the second plate (40). Preferably, the first mechanism (60) comprises a screw (62) operatively connected to the first plate (30), more particularly to the tenon (38) in which it extends longitudinally and only rotates on itself with reference to it. The screw (62) is in mesh with a corresponding threaded element (64) rigidly attached to the second plate (40). Because the screw (62) extends in the tenon (38), the tenon (38) has a longitudinal opening (66) to allow the screw (62) to reach the threaded element (64) and to allow the tenon (38) to slide in spite of the presence of the threaded element (64) (see FIG. 6). The screw (62) may be operated by means of the thumbscrew knob. Providing the screw (62) with very fine threads generates a self-locking mechanism that will not move unless the screw (62) is operated on purpose.

Figure 5:
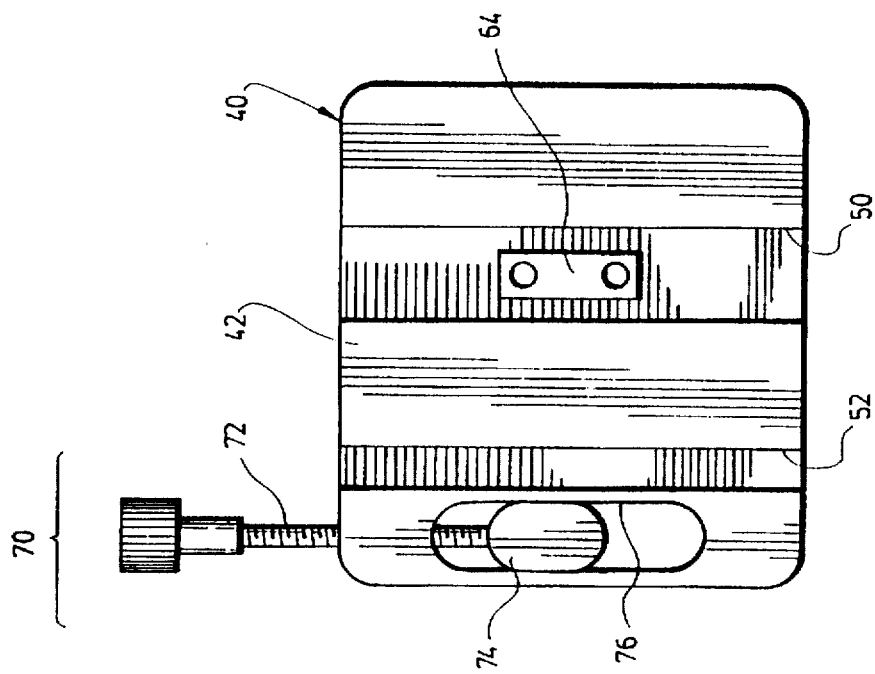
FIG. 5 is a top view of the second plate shown in FIG. 4.
Figure 6:
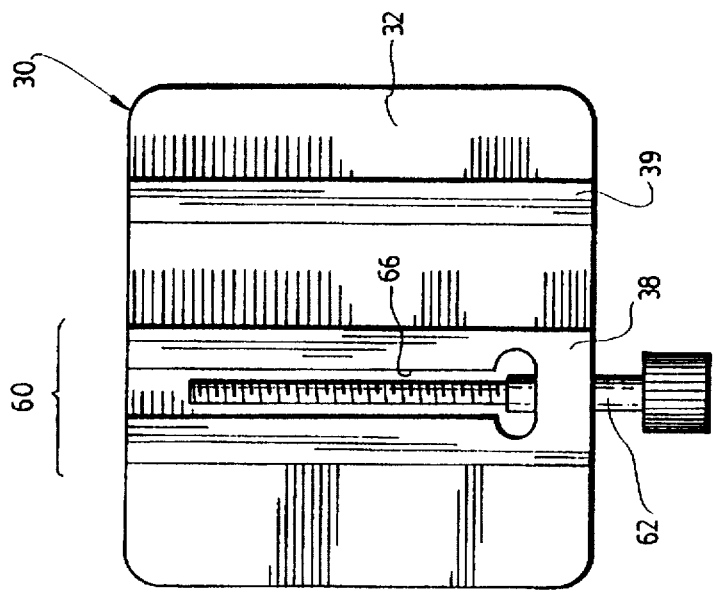
FIG. 6 is a bottom view of the first plate of the mounting device shown in FIG. 1.

The rotation and locking of the device (20) with reference to the articulator (10) is achieved by a second mechanism (70). Preferably, as shown in FIG. 5, the second mechanism (70) comprises a screw (72) in mesh with a lateral side of the second plate (40) and operatively connected to a holding element (74). The holding element (74) is located at a free end of the screw (72) inside a slot (76) in the second plate (40). The holding element (74) is connected to a fixed location, for example to one of the alignment pegs (18) usually already provided on the articulator (10) (see FIG. 7). To prevent the other peg (18) from interfering, if any, there is provided a wide opening (48) in the second side (44) of the second plate (40) so that the latter may be pivoted freely within the desired range of angles. Like the screw (62) of the first mechanism (60), the screw (72) may be operated by means of a thumbscrew knob and providing it with very fine threads generates a self-locking mechanism that will not move unless the screw (72) is operated on purpose.

In order to keep track of the translation and the rotation, the mounting device (20) may further comprise a first graduated scale (80) for measuring displacements of the first plate (30) relative to the second plate (40), and a second graduated scale (82) for measuring angular displacements of the second plate (40) relative to the dental articulator (10). Preferably, each of these scales (80, 82) comprises a vernier (80A, 80B, 82A, 82B) to increase accuracy in the measurements.

The embodiment described hereinabove comprises two degrees of freedom, but there are additional embodiments with only one degree of freedom. For instance, it is possible to provide only the second plate (40) without the first plate (30). In that case, the first side (42) of the second plate (40) has the recesses (36).

Another possible embodiment is the one where the first (30) and the second plate (40) are provided, but only the first mechanism (60) is present, the second plate (40) being fixedly connected to the articulator (10) like in the prior art.

Moreover, it is possible to superpose more than two plates and provide additional mechanisms to add other degrees of freedom, such as additional sliding directions in the horizontal plane.

Although preferred embodiments of the invention have been described in detail herein and illustrated in the accompanying drawings, it is to be understood that the invention is not limited to these precise embodiments and that various changes and modifications may be effected therein without departing from the scope or spirit of the invention.

What is claimed is:

1. An adjustable mounting device for use with a dental articulator of the type having two opposite arms, at least one arm being provided with a pivot screw and an adjacent peg, the mounting device comprising:

a first plate having opposite first and second sides;

a second plate having opposite first and second sides, the first side of the first plate being superposed on the first side of the second plate and in a sliding relationship therewith, the second side of the second plate comprising a threaded pivot bore for receiving the pivot screw of the dental articulator;

a first screw mechanism to selectively slide and lock in position the first plate relative to the second plate, the first mechanism comprising a first screw operatively connected either to the first or the second plate and in mesh with a threaded element rigidly attached respectively to the second or the first plate so that the first plate is slid relative to the second plate upon rotation of the first screw;

a second screw mechanism to selectively rotate and lock in position the second plate relative to the dental articulator, the second mechanism comprising a second screw in mesh with the second plate and operatively connected to a holding element located at one free end of the second screw, the holding element being connected to one peg of the dental articulator so that the second plate is pivoted relative to the dental articulator upon rotation of the second screw;

a first graduated scale for measuring displacements of the first plate relative to the second plate; and a second graduated scale for measuring angular displacements of the second plate relative to the dental articulator.

2. An adjustable mounting device according to claim 1, wherein the second side of the second plate comprises an opening to accommodate a second peg adjacent the pivot screw of the arm of the articulator so that the second plate be rotated freely with a range of angles.

3. An adjustable mounting device according to claim 1, wherein each of the first and second graduated scales comprises a vernier.

* * * * *